(12) United States Patent
Kruse et al.

(10) Patent No.: US 8,546,117 B2
(45) Date of Patent: Oct. 1, 2013

(54) METHOD AND DEVICE FOR FORMING A THREE-DIMENSIONAL ARRANGEMENT OF BIOLOGICAL CELLS

(75) Inventors: Charli Kruse, Herrnburg (DE); Philipp Ciba, Luebeck (DE); Guenter Fuhr, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 632 days.

(21) Appl. No.: 12/664,933

(22) PCT Filed: Jun. 6, 2008

(86) PCT No.: PCT/EP2008/004538
§ 371 (c)(1),
(2), (4) Date: Dec. 16, 2009

(87) PCT Pub. No.: WO2008/155028
PCT Pub. Date: Dec. 24, 2008

(65) Prior Publication Data
US 2010/0190249 A1  Jul. 29, 2010

(30) Foreign Application Priority Data
Jun. 20, 2007 (DE) .......................... 10 2007 028 422

(51) Int. Cl.
*C12N 11/00* (2006.01)
*C12N 11/16* (2006.01)
*C12P 1/00* (2006.01)

(52) U.S. Cl.
USPC ............................................ 435/174; 435/41

(58) Field of Classification Search
USPC .................................................. 435/41, 174
See application file for complete search history.

(56) References Cited

U.S. PATENT DOCUMENTS
2002/0182241 A1* 12/2002 Borenstein et al. ........... 424/422
2004/0033482 A1   2/2004 Artmann
2006/0194309 A1   8/2006 Fuhr et al.

FOREIGN PATENT DOCUMENTS
WO       0218937 A1      3/2002
WO     2004046337 A2    6/2004
WO     2004074425 A2    9/2004

OTHER PUBLICATIONS

Balaban et al. "Force and focal adhesion assembly: a close relationship studied using elastic micropatterned substrates" *Nature Cell Biology* vol. 3, May 2001, 466-472, plus supplementary p. 1.*
Balaban et al., "Force and focal adhesion assembly: a close relationship studied using elastic micropatterned substrates", Nature Cell Biology, vol. 3 (2000), pp. 466-473.
Bischofs et al., "Cell organization in soft media due to active mechanosensing", PNAS, vol. 100 (2003), pp. 9274-9279.
Brandl et al., "Rational design of hydrogels for tissue engineering: Impact of physical factors on cell behavior", Biomaterials, vol. 28 (2007), pp. 134-146.
Burton et al., "Keratocytes Generate Traction Forces in Two Phases", Molecular Biology of the Cell, vol. 10 (1999), pp. 3745-3769.
Curtis et al., "Measuring Cell Forces by a Photoelastic Method", Biophysical Journal, vol. 92 (2007), pp. 2255-2261.
Harris, Jr., "Tissue Culture Cells on Deformable Substrata: Biomechanical Implications", Journal of Biomechanical Engineering, vol. 106 (1984), pp. 19-24.
Lo et al., "Cell Movement is Guided by the Rigidity of the Substrate", Biophysical Journal, vol. 79 (2000), pp. 144-152.
Nicolas et al., "Dynamics of Cellular Focal Adhesions on Deformable Substrates: Consequences for Cell Force Microscopy", Biophysical Journal, vol. 95 (2008), pp. 527-539.

* cited by examiner

*Primary Examiner* — Jon P Weber
*Assistant Examiner* — Thane Underdahl
(74) *Attorney, Agent, or Firm* — Caesar, Rivise, Bernstein, Cohen & Pokotilow, Ltd.

(57) ABSTRACT

A method for forming a three-dimensional cell arrangement (1) of biological cells is disclosed, including the steps of preparation of the cell arrangement (1) on a flexible substrate (10) and deformation of the substrate (10), wherein the deformation of the substrate (10) is brought about by an attractive force exerted by the cells (2) on the substrate (10). A substrate (10), is also disclosed, made from a flexible material and including a substrate surface (11) for adhesion of a cell arrangement (1) of biological cells, wherein the substrate surface (11) has a number of force attachment points arranged to exert an attraction force which may be transmitted from the cells to the substrate (10) and the substrate (10) has a flexibility such that the substrate (10) is deformable with the action of the attraction force.

13 Claims, 6 Drawing Sheets

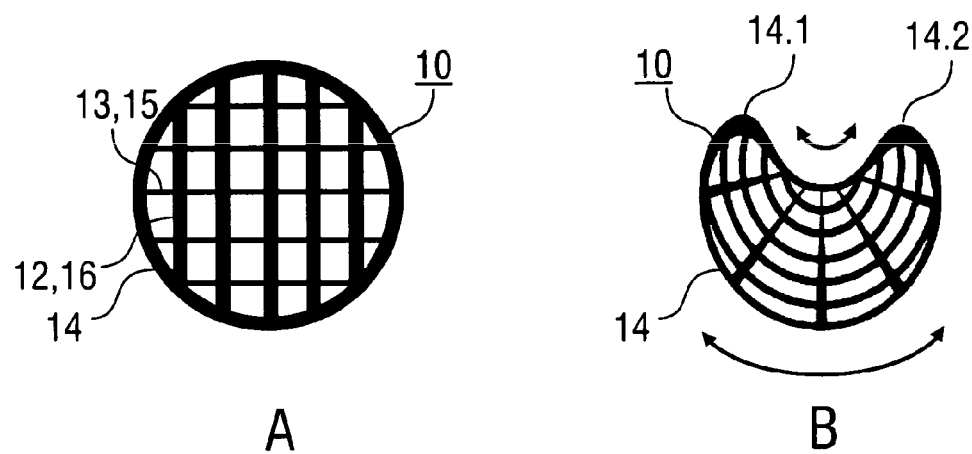
FIG. 4
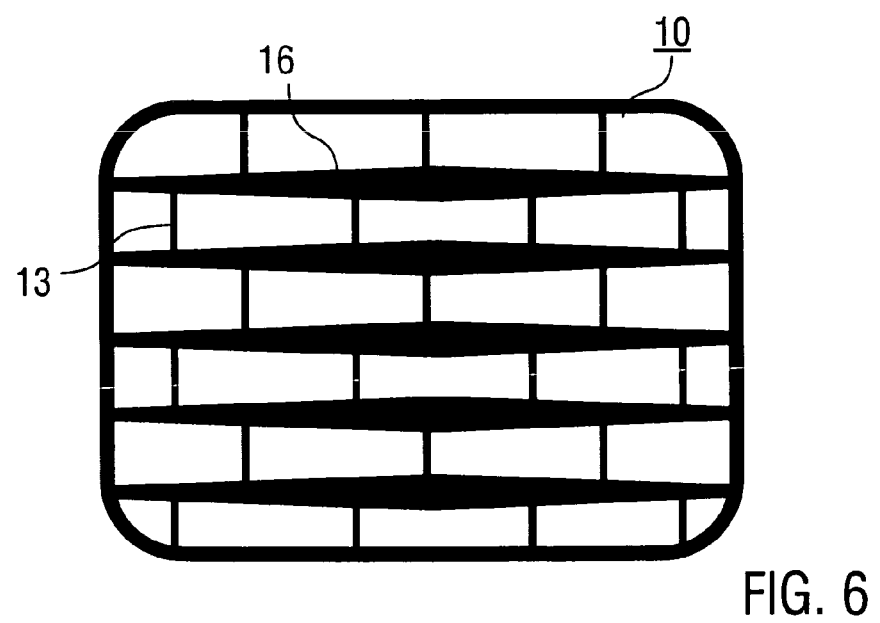
FIG. 5
FIG. 6

A

B

C

D

METHOD AND DEVICE FOR FORMING A THREE-DIMENSIONAL ARRANGEMENT OF BIOLOGICAL CELLS

BACKGROUND OF THE INVENTION

The invention relates to a method for forming a three-dimensional cell arrangement having a plurality of biological cells, in particular a method for setting or varying a geometric spatial configuration of a cell arrangement and methods for geometrically structuring cell material such as, for example, methods for so-called tissue engineering. The invention also relates to a device for carrying out these methods, in particular a substrate for a cell arrangement such as, for example, a cell culture or tissue, with which the geometric spatial configuration of a cell arrangement is adjustable or variable. The invention also relates to uses of the method and of the device.

In cell biology, biological cells typically undergo culturing (growth and/or differentiation) in an adherent state on a plane substrate. The advantage of culturing on the substrate is that the cells can then be adequately supplied with nutrients and the cells can be observed, e.g. using a microscope. One disadvantage is, however, that the adherent state on a substrate does not correspond to the conditions under which the cells naturally live. In the living organism, in particular in the living animal or human organism, cells form three-dimensional cell arrangements such as, for example, tissue or organs. In a three-dimensional cell arrangement the formation of cell-cell contacts in space means that the cells live under conditions different from those on a plane substrate. There is therefore interest in synthetically reproducing three-dimensional cell arrangements, in particular for purposes of the in vitro study of biological cells or medical cell therapy or tissue processing, in particular tissue engineering.

WO 2004/046337 proposes reproducing a three-dimensional cell arrangement by means of a structure consisting of layers of cells and biopolymer. In this structure the cells are spatially distributed in the biopolymer. One disadvantage of this technique is that conditions under which the cells naturally live can be created only to a limited extent. The biopolymers do not form the typical environment of the cells in living organisms. Further disadvantages are the limited shaping variability for the cell arrangement and the limited nutrient supply of the cells embedded in the biopolymer.

WO 2004/074425 discloses a method for geometrically forming cell material using an adjustable manipulation tool. A variant of this method is shown in FIG. 13. The cell material 1' having a plurality of biological cells 2' is arranged on a layered flexible substrate 10'. The shape of the substrate 10' is variable with a drive apparatus 30' and a plurality of shaping elements 31'. The substrate 10' with the cell arrangement 1' is arranged in a culturing vessel 40' containing a culturing liquid 41'. The shape of the substrate 10' can be set by displacing the shaping elements 31', such that the cell material can be formed with a curved surface.

The practical use of the technique described in WO 2004/074425 may be limited as a result of the following disadvantages. First, engineering freedom is restricted by the movement of the shaping elements 31'. The drive apparatus 30' cannot be used, for example, to create niches or cavities, yet these are of great interest for the replication of natural culturing conditions. Furthermore, the cells can grow only on the upper substrate face, since the lower substrate face is necessarily in contact with the shaping elements 31'. This gives rise to limitations in terms of the nutrient supply to the cells. Furthermore, the substrate can disrupt the natural culturing conditions of the cells in the cell material.

It is known from cell biology that cells exert attractive forces on substrates. US 2004/0033482 A1 proposes measuring the attractive forces by culturing cells on a pre-tensioned curved substrate. As a result of the attractive forces the substrate is bent back counter to the curvature, and curvature compensation is evaluated as a measure for the attractive forces.

The objective of the invention is to provide an improved method for forming a three-dimensional cell arrangement from biological cells, a method with which disadvantages of the conventional techniques are avoided and which, in particular, allows improved replication of conditions under which cells naturally live. A further objective of the invention is to provide an improved device for forming a three-dimensional cell arrangement with which limitations of the conventional techniques are overcome and which, in particular, has a widened field of use.

These objectives are achieved with a method and a device having the features of the invention.

SUMMARY OF THE INVENTION

According to a first aspect, the invention is based on the general technical teaching of forming a three-dimensional cell arrangement by arranging, on a flexible substrate, biological cells which exert a force (attractive force) thereon. The inventors found that adherent cells exert, directly onto the substrate surface, a mechanical tension under the action of which the flexible substrate changes shape. This endogenous attractive force of the cells is formed by compressive and/or tensile forces caused by the internal cytoskeleton and intermolecular interactions (bonds) between surface molecules of the cells and the substrate surface.

The attractive force proved to be strong enough to cause flexible substrates to change shape. Although it is already known that cells can move as a result of the intermolecular interaction on substrate surfaces, the substrate deformation according to the invention constitutes a surprising outcome since not only cells (that is to say microscopic particles) but also the substrate, with macroscopic dimensions, is deformed by the cell forces. Thus the force exerted by a cell on a substrate is 1 pN to 5 pN per bond. It is possible for a few thousand, e.g. 2000, to one or more million bonds to be formed, so that the attractive force per cell is 1 nN to 1 µN. With a thousand or more cells on the substrate the attractive force is, for example, up to 1 mN.

According to a second aspect of the invention, the above-mentioned objective is achieved by the general technical teaching of providing a substrate which is made from a flexible material and the substrate surface of which is adapted for receiving biological cells, with the substrate surface being adapted for the formation of intermolecular interactions (molecular bonds) with the cells and for receiving the attractive force exerted by the cells on the substrate, such that the substrate is deformable under the action of the attractive force. The substrate is deformable as a result of the action of the attractive force thereon. With the deformation of the substrate, the cell arrangement is formed in space.

Flexibility generally indicates the property of a body to yield to a force (tension or pressure) by means of a shape change. The substrate according to the invention has such a flexibility that, under the action of the attractive force of the cells, the substrate is, in particular, plastically or elastically deformable. The substrate according to the invention is, at least sectionally, made from a material in which a force in opposition to the deformation (in particular, internal frictional force or elastic resilience) is less than the attractive force. In the case of elastic deformability, the substrate has such low flexural rigidity that it is deformable under the action of the attractive force. The deformation comprises, in particular, an increasing bending of the substrate.

The shape change of the substrate is brought about, in particular, by virtue of the attractive force acting on different action points with different orientations (tension). The substrate is, for example, distorted in dependence on the directions of the attractive force. The substrate surface of the substrate according to the invention has a plurality of force action points which are adapted for exposure to the action of the attractive force. The force action points are preferably formed as locally limited parts of the substrate surface.

The force action points (force action regions) are local surface regions adapted for intensified intermolecular interaction between the cells and the substrate surface and thus for local exertion of the attractive force. Force action points are distinguished by cell adhesion greater than that over the remaining substrate surface. A texture of the substrate surface or a chemical modification of the substrate surface is, for example, provided for this purpose. The force action points comprise, in particular, adhesive structures and/or adhesive coats which are arranged in or on the substrate surface with a predetermined geometric distribution. Adhesive structures are formed, for example, by edges, steps and/or holes in the substrate surface such as, for example, lattice elements. Adhesive coats comprise, for example, fibronectin, collagen or other biomaterials or a surface coverage functionalized with macromolecules.

The term "cell arrangement" here designates a composition being made of a plurality of biological cells of the same or different cell types and being arranged in a distributed manner on the surface of the substrate. The cell arrangement comprises a continuous layer of cells on the substrate surface or alternatively an arrangement of cell groups which are mutually spaced apart. According to a preferred embodiment of the invention, the cells form the continuous layer of cells and the attractive force is transmitted from the cells directly onto the substrate surface. In this case the result is advantageously a particularly effective deformation of the substrate. A layer of cells can, for example, comprise a single monolayer or a plurality of cell layers (at least two monolayers). Preferred uses of the three-dimensional cell arrangement formed according to the invention are in medical therapy and in technical applications for biological cells.

The invention has the following advantages. The formation of the cell arrangement with the substrate enables defined three-dimensional multicellular structures to be produced. The substrate is deformed as the cells apply mechanical work on the substrate surface. The speed of substrate deformation is determined by the speed of the redistribution of molecular bonds between the cells and the substrate surface. This speed substantially corresponds to the natural motion rate of adherent cells. The speed of substrate deformation is thus determined by physiological cell properties, so it is possible to avoid substrate deformation having a disruptive effect on the cell arrangement.

A further advantage is that substrate deformation can generally take place without extensive contact between the substrate and a deformation tool such as, for example, the conventional shaping elements. The attractive force is exerted without a mechanical tool coming into contact with the substrate. Thus the substrate can be formed with a more complex volumetric topography than in the conventional techniques. Furthermore, cells of the same or different cell types can be arranged on all faces of the substrate.

A further advantage arises from the variability of the substrate configurations that are selectable according to the invention. For example, according to a first variant a curvature of the substrate can be provided such that a layered cell arrangement is formed with a spatial curvature. The layered cell arrangement (layer of cells) can comprise a monolayer or a multilayer of the biological cells, with the geometric extension of the layer of cells being represented by a spatially curved face. Advantageously, it is thus possible to replicate three-dimensional cell structures such as occur in living organisms, with a free nutrient supply guaranteed over the entire curved surface of the layer of cells. According to a second variant, the substrate can be folded, in which case the substrate is bent to such an extent that at least two sections of the substrate surface are disposed opposite each other. The perpendicular distance between the sections of the substrate surface becomes so small that the cells on the sections are in mutual contact or can close the distance by virtue of cell growth. Folding of the substrate causes the cell arrangement to form a three-dimensional pile of cells. Unlike with the conventional formation of layers of cells and biopolymer, the three-dimensional pile of cells can be a loose composition. The pile of cells is permeable to gaseous and liquid media, in particular for the supply of nutrients. According to a further variant, the spatially curved layer of cells and the three-dimensional pile of cells can be combined by one part of the substrate becoming curved and another part of the substrate being folded.

For the formation of the force action points the substrate according to the invention preferably has, at least in one section, a lattice structure (framework structure) with a plurality of lattice elements. The force action points of the inventive substrate having the lattice structure (hereinafter referred to as "lattice substrate") are formed on the lattice elements. The inventors found that the lattice structure also provides a substrate surface on which can be formed a continuous cell arrangement which spans holes in the lattice structure and exerts the attractive force of the cells particularly effectively. The holes are formed between the lattice elements. The holes may have a characteristic dimension (for example side length, diameter) greater than the size of an individual cell. The lattice substrate can therefore have a lattice structure which allows the cells to grow right round the substrate.

The lattice structure is not mandatory. If, alternatively, a continuous substrate surface with interruptions, for example trenches or depressions, is provided, this likewise has advantages for the formation of the force action points.

Alternatively or in addition the substrate has, at least in one section, a continuous substrate surface on which the force action points are formed. The continuous substrate surface which, without the exertion of attractive force, is preferably plane, has advantages for the formation of a completely covering cell arrangement and thus of enhanced effectiveness of the attractive force of the cells.

Continuous substrate surfaces have advantageous uses as coverage for implantation or wound healing purposes. The substrate according to the invention may, for example, allow the provision of a wound cover film with a curvature corresponding to the surface of the wound to be covered and having a cell arrangement (for example, consisting of keratinocytes, skin stem cells, endothelial cells, epithelial cells, skin cells differentiated from stem cells and/or other tissue-type cells) with which wound healing is accelerated.

According to a preferred embodiment of the invention, there is provided a directional deformation of the substrate where the substrate surface undergoes curvature in at least one predetermined main deformation direction. The substrate has at least one preferred direction of deformation, that is to say, in at least one direction the substrate has less flexural rigidity than in other directions. Advantageously, the shape of the cell arrangement formed according to the invention can be selectively determined by engineering (architecture) of the substrate. The at least one main deformation direction is preferably defined by the geometric distribution of predetermined deformation regions of the substrate and/or of the force action points. Advantageously, the nature of the cell arrangement (curved layer of cells or three-dimensional pile of cells) and the geometric configuration thereof can thus be selected in dependence on the specific use of the invention.

For forming the at least one main deformation direction the substrate according to the invention preferably has anisotropic and/or locally variable flexibility (in particular, flexural rigidity). The substrate has predetermined deformation regions of increased or reduced flexural rigidity. The deformation regions comprise bending or stiffening regions in which the substrate has reduced or increased flexural rigidity by virtue of a suitable choice of substrate material or according to the substrate structure concerned. Alternatively or in addition to the provision of the deformation regions, the main deformation direction can be determined by an irregular geometric distribution of the force action points on the substrate surface.

The lattice substrate according to the invention has particular advantages for the selection of anisotropic and/or locally variable flexibility and for the effective exertion of the attractive force of the cells. The flexibility of the lattice substrate can be selected by means of the distribution, the alignment, the material and/or the dimensions (diameter, length) of the lattice elements.

The substrate according to the invention with deformation regions and/or inhomogeneously distributed force action points advantageously constitutes a new cell biology tool with which cells can form three-dimensional cell arrangements on the basis of endogenous cell forces. The configuration, structure and/or composition of the cell arrangement can be reproducibly preset by means of the substrate.

According to a further preferred embodiment of the invention, the at least one main deformation direction is selected such that the deformed substrate forms a cavity. Advantageously, a niche formed in natural tissue or in organs such as, for example, a gland structure or a vessel can thus be appropriately replicated. Thus a tubular shape or a spherical shape is particularly preferred, since these are adapted to the topology of natural cell structures. Alternatively, other spatial configurations such as, for example, helixes or compact geometries such as, for example, spheres, ellipsoids or toroids can be formed.

According to a further advantageous embodiment of the invention, the substrate can have at least one substrate part, the position and/or orientation of which relative to the remaining substrate, for example further substrate parts or a substrate body, is varied by deformation. The substrate particularly preferably comprises a plurality of substrate parts, in particular substrate layers (substrate plys), which, as a result of the shape change of the at least one substrate part, are differently deformable and/or mutually separable. Advantageously, this further increases variability when the cell arrangement is formed as a curved layer of cells or as a three-dimensional pile of cells is thus.

The substrate particularly preferably comprises a stack of substrate layers. The substrate layers, for example made from plastics films, are disposed one above the other. According to the invention the cell arrangement can, in a first step, be arranged on the uppermost substrate layer, which is deformed under the action of the attractive force of the cells. The deformed substrate layer exposes the surface of the substrate layer which is disposed therebelow and which, after cells have been arranged in a second step, is likewise deformed. The cells can be arranged on the lower-lying substrate layer by means of natural cell migration or by the deposition of further cells. As a result, the substrate layers undergo different shape changes, and thus cells forming a three-dimensional pile of cells are arranged between the substrate layers. Alternatively, substrate layers can be separated from the remaining substrate and subjected to further cell biology methods.

Advantageously, the method according to the invention for forming a three-dimensional cell arrangement can be combined with further cell biology methods. For example, culturing of the cells, comprising in particular growth of the cell arrangement and/or differentiation of the cells, can take place. Culturing of the cells particularly preferably takes place on the still undeformed substrate and/or during deformation of the substrate with the formation of the cell arrangement. Advantageously, the formation of a three-dimensional cell arrangement according to the invention can comprise a first phase of culturing in conventional culturing apparatus, in particular on a plane substrate, and a second phase in which the desired three-dimensional configuration of the cell arrangement is formed. Deformation of the substrate preferably takes place only after the cells are cultured on the substrate surface, particularly preferably after the cells have fully grown on the substrate surface or after a continuous layer of cells has formed on the substrate. The cells are thus initially propagated in a two-dimensional form and then the cell arrangement is brought into the desired shape. The shape is thus preferably determined by the substrate.

According to a further variant of the invention, the formation of the three-dimensional cell arrangement can be combined with a supply of further cells to the cell arrangement. The three-dimensional cell arrangement can be used as a culturing substrate for further cells. For example, stem cells can be deposited on a three-dimensional structure of differentiated cells and can undergo further culturing, in particular differentiation.

Furthermore, following the formation of the three-dimensional cell arrangement the latter can be separated from the deformed substrate. If the substrate is dissolved and/or mechanically removed from the cell arrangement, a three-dimensional cell arrangement consisting solely of biological cells and free from non-natural substrate materials will advantageously be formed.

According to a further embodiment of the invention, it is possible to form a plurality of three-dimensional cell arrangements using separate substrates and then to combine the separately produced cell structures. Advantageously, the size and shape of the cell arrangement can thus be freely selected. This is advantageous for implantation uses in particular.

According to a further embodiment of the invention, the action of the attractive force of the cells can be assisted by an additional deformation force which comprises an external mechanical force and/or an internal reaction force in the substrate material. The external mechanical force is exerted using a deformation tool which, unlike in conventional techniques, does not require plane contact with the substrate. It is sufficient for the external mechanical force to be exerted at individual positions of the substrate. The internal reaction force in the substrate material comprises, for example, an inner tension generated by the structure of the substrate material. The internal reaction force is preferably activated by a mechanical, chemical, thermal, electrical and/or optical action.

The variable design of the substrate according to the invention is a further advantage of the invention. For example, the substrate is made from plastic or metal. Biocompatible and chemically inert materials are preferred. If the substrate is made from a resorbable material, for example fibrin, the substrate can advantageously be dissolved following the formation of the three-dimensional cell arrangement.

According to a further embodiment of the invention, the substrate surface can have a modification layer. The modification layer is made from at least one biologically active substance such as, for example, a differentiation factor, or from a pharmacologically active substance or biological cells. Advantageously, the modification layer enables the cells in the cell arrangement to be influenced.

According to a further aspect, the above-mentioned objective of the invention is achieved by means of a composition of a flexible substrate and a cell arrangement of biological cells, with the substrate being deformed under the action of the attractive force ($F_z$) of the cells.

The use of a flexible substrate for forming a three-dimensional cell arrangement constitutes a further independent subject of the invention.

BRIEF DESCRIPTION OF SEVERAL VIEWS OF THE DRAWINGS

Further details and advantages of the invention will become apparent from the description of the accompanying drawings, which show in:

FIGS. 4 to 9: further embodiments of substrates according to the invention;

DETAILED DESCRIPTION OF PREFERRED EMBODIMENTS

Figure 1:
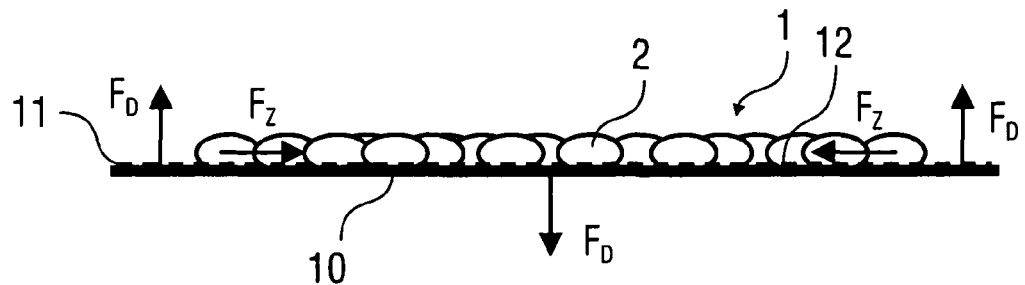
FIGS. 1 to 3: diagrammatic illustrations of the formation, according to the invention, of a three-dimensional cell arrangement.

FIG. 1 illustrates a first embodiment of a substrate 10 according to the invention in a diagrammatic sectional view. The substrate 10 is made from a flexible, elastically or plastically deformable material such as, for example, plastic, cellulose, a polymer, a textile material such as, for example, a woven fabric, a knit fabric or the like, a noble metal or a resorbable material. The substrate has a two-dimensional (planar) extension, thus taking the form of a film (layer, sheet or platelet) or lattice (framework, net). On a surface 11 which is provided for receiving the cell arrangement 1 consisting of biological cells 2, the substrate 10 has force action points 12. The force action points 12 of the substrate surface 11 comprise, for example, roughened regions or chemically modified regions which are occupied by biologically active molecules forming bonds with cell surface receptors. The shape of the regions can be freely selected. The force action points 12 may, for example, comprise circular areas, rectangles or straight or curved lines.

The dimensions of the substrate 10 and the shape and alignment of the force action points 12 are selected in dependence on the desired deformation of the substrate 10. The thickness of the substrate is selected such that sufficiently low flexural rigidity is achieved for deformation of the substrate 10 under the action of the attractive force ($F_z$) of the cells. A thickness can, in particular, be selected by means of a series of tests with different layer thicknesses under the specific conditions of use. Along the extension of the substrate 10 the thickness can be a reduced thickness for forming deformation regions of increased flexibility (bending region). Typically the thickness of the substrate 10 for plastics or metal substrates is selected in the range below 10 nm to 3 mm, in particular below 100 µm. The lateral dimension (side length, circumference) and shape of the substrate 10 is likewise selected in dependence on the specific use.

FIG. 1 shows the substrate 10 in the state prior to the start of the deformation according to the invention. In this state the substrate 10 preferably has a plane form, in particular with a plane substrate surface. Notwithstanding the variant shown in FIG. 1, the substrate 10 can already have a curved shape before deformation (see, for example, FIG. 7).

The cells 2 are adherently arranged on the substrate surface 11. The cells 2 comprise, for example, animal cells, in particular differentiated cells, such as, for example, fibroblasts, muscle cells, epithelial cells and/or endothelial cells, or precursor cells such as, for example, hematopoietic precursor cells, progenitor cells and/or blast cells, or embryonic or adult stem cells. The cells 1 form the layered cell arrangement 2, which forms continuous coverage of the substrate surface 11. The layered cell arrangement 2 can comprise a plurality of cell layers. The thickness of the cell arrangement 2 is, for example, 1 mm. The adherent cells 1 form intermolecular interactions between the cell membrane and the substrate surface 11. With the substrate surface 11 the cell membrane forms adhesion contacts which, owing to the ongoing rearrangement of the cytoskeleton of the cells, undergo repeated change. At the same time there take place, between the cells 2, intermolecular interactions leading to cohesive bonds between the cells. The inventors found that the cohesive bonds may be strong enough to generate the attractive force under the action of which the substrate 10 is deformed. The attractive force exerted tangentially to the substrate surface is shown in FIG. 1 diagrammatically as $F_z$. In addition to the attractive force $F_z$ it is possible for a locally acting deformation force $F_D$ to be exerted with an external tool (not shown) on the substrate 10 at least at one position, to assist the action of the attractive force.

For carrying out the method according to the invention the substrate 10 is arranged in a culturing apparatus in a culturing liquid. Details of the culturing apparatus are described below with reference to FIG. 12. Cells 2 are applied to the substrate 10 and undergo culturing until the cell arrangement 1 is formed. Culturing takes place under the usual culturing conditions, as known from the techniques of cell biology. As soon as the attractive force of the cells 2 is sufficiently great, deformation of the substrate 10 begins. In dependence on the local distribution of flexibility of the substrate 10, the latter undergoes bending or folding, as shown by way of example in FIGS. 2 and 3. The speed of deformation is determined by the speed of the rearrangement of molecular cell contacts in the cell arrangement and/or by the culturing speed of the cell arrangement. Complete deformation can take place, for example, in a time interval of days to weeks. Deformation ends, in particular, if a counterforce formed by the substrate forms an equilibrium with the attractive force exerted by the cell forces. To achieve a desired aim (for example, a curvature, a thickness of the cell arrangement, a tubular shape, a cavity or the like), the material and the geometry of the substrate and, in particular, of the force action points are selected as appropriate. Alternatively or in addition, deformation can be terminated by dissolution of the substrate or removal of the substrate with the cells from a culturing medium (cell proliferation medium).

Figure 2:
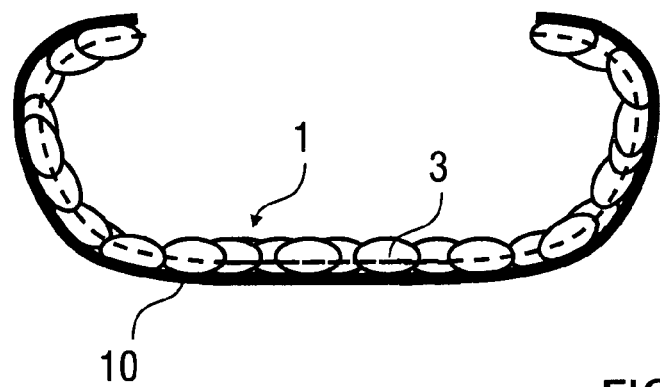
Figure 3:
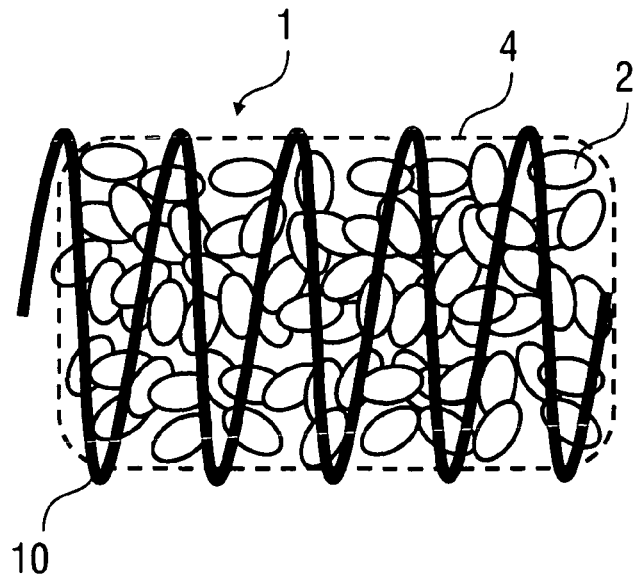

With a substrate 10 having a gradient of flexibility diminishing towards the borders, the attractive force of the cells gives rise to the substrate curvature illustrated diagrammatically in FIG. 2. The cell arrangement 1 forms a curved layer of cells 3 which extends along a spatially curved face (broken line). A substrate 10 having, on both surfaces, force action points and an arrangement of parallel linear bending regions gives rise to the substrate folding shown in FIG. 3. The cells 2 of the cell arrangement 1 form a three-dimensional pile of cells 4. The folded substrate 10 is incorporated in the pile of cells 4. Where a resorbable material is used, the folded substrate 10 can be dissolved in the course of the further culturing of the cells 2 in the pile of cells 4.

Directional deformation of the substrate is also possible if the cells have grown on both surfaces of the substrate (e.g. of a lattice substrate). The direction of curvature can be determined by differences in growth on the two surfaces. These differences may be fortuitous or specifically selected by virtue of the provision of different quantities of cells on the surfaces. Furthermore, the attractive force of the cells on one of the surfaces can be varied by a supply of particles which control the cell forces, in particular nanobeads or microbeads, on one of the surfaces in order to control the direction of curvature. Finally, the direction of curvature can be selected by means of material properties of the substrate (in particular, selection of the main deformation direction).

Further examples of substrates 10 according to the invention and having a lattice structure (lattice substrates) are illustrated in FIGS. 4 to 9. A substrate 10 having a lattice structure generally comprises a plurality of lattice elements 13 surrounded by a lattice frame 14 (see, for example, FIG. 4A). The form of the lattice frame 14 may have a simple geometric shape (for example, a circle or rectangle, see FIGS. 4 to 7) or a more complex shape (see FIGS. 8, 9). For the sake of clarity the lattice substrates are all shown without the cell arrangement, except in FIG. 9C.

The lattice elements 13 and the lattice frame 14 are formed such that the substrate 10 has a predetermined main deformation direction. According to FIG. 4A there are, for example, provided in a first direction (longitudinal direction) more rigid (thicker) lattice elements which also form the force action points 12 and the stiffening regions 16. Lattice elements 13 (bending regions 15) with less flexural rigidity are also provided in a second direction (transverse direction). The lattice substrate 10 according to FIG. 4A thus has less flexural rigidity in a transverse direction than in a longitudinal direction.

The formation of a continuous cell arrangement on the lattice substrate 10 causes said substrate to be deformed. A curvature is produced, depending on the direction of reduced flexural rigidity. The curvature may be produced by opposite edges 14.1, 14.2 of the lattice frame 14 coming into mutual contact and by a continuous, three-dimensional shape, e.g. a pocket or niche, being formed (FIG. 4B).

FIG. 5 shows a further example of a lattice substrate 10 having a plurality of parallel lattice elements 13 and having a lattice frame 14, the outer edge of which is provided with stiffening regions 16. The lattice elements 13 also form the force action points of the lattice substrate 10. The purpose of the stiffening regions 16 is to control the shape when the substrate 10 is deformed. In the case of the lattice substrate 10 according to FIG. 5, the complex superimposition of the action of the lattice elements 13 and of the stiffening regions 16 gives rise to a plurality of main deformation directions.

The stiffening regions 16 can alternatively or additionally be provided on the lattice elements 13, as shown by way of example in FIG. 6. In a first direction (longitudinal direction) the lattice elements 13 are not very thick and accordingly have low flexural rigidity. In a second direction (transverse direction) the lattice elements have a thickened portion for forming the stiffening regions 16. Increased flexural rigidity is to be found. The main deformation direction of the substrate 10 according to FIG. 6 is thus preset by the low flexural rigidity in a longitudinal direction.

Figure 7:
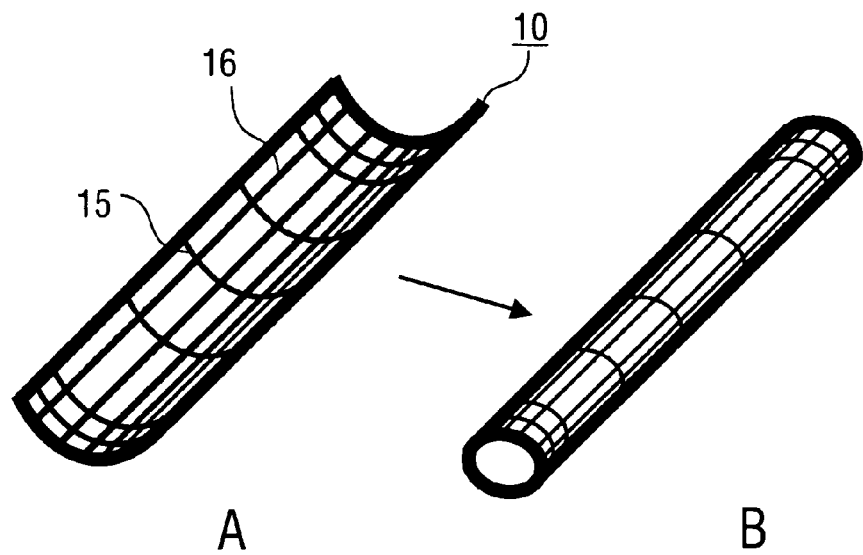

FIG. 7A shows, by way of example, an embodiment of a lattice substrate 10 having a curved pre-form even prior to the exertion of the attractive force of the cells. The lattice substrate 10 forms the portion of a periphery of a straight regular cylinder. The lattice elements in an axial direction are thicker (stiffening regions 16) than the lattice elements in an azimuthal direction (bending regions 15). After overgrowth with a cell arrangement, the lattice substrate 10 is curved further by virtue of the attractive force until the tubular or tube-like shape according to FIG. 7B is produced. The embodiment of the invention shown in FIG. 7 has particular advantages for the replication of biological organs or parts of organs for conveying liquids such as, for example, tubes or vessels, in particular blood vessels.

Figure 8:
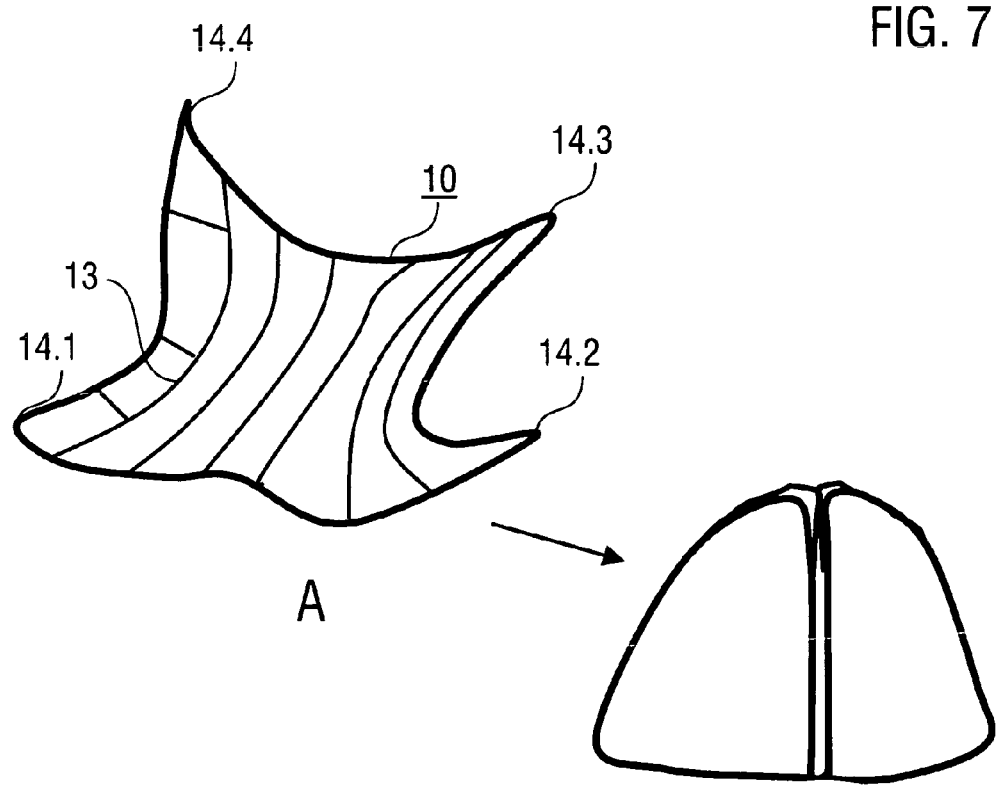

The embodiment of the lattice substrate 10 shown in FIG. 8 has a more complex shape with a plurality of main deformation directions. Under the action of the attractive force of the cells, the lattice frame 14 of the lattice substrate 10 undergoes curvature such that mutually opposite border regions, in particular the corner regions 14.1 to 14.4, come into mutual contact (FIG. 8B). Advantageously, this creates a cavity that can be used as a substrate niche for culturing cells of the cell arrangement arranged on the substrate or for culturing additionally supplied cells, for example a stem cell.

Figure 9:
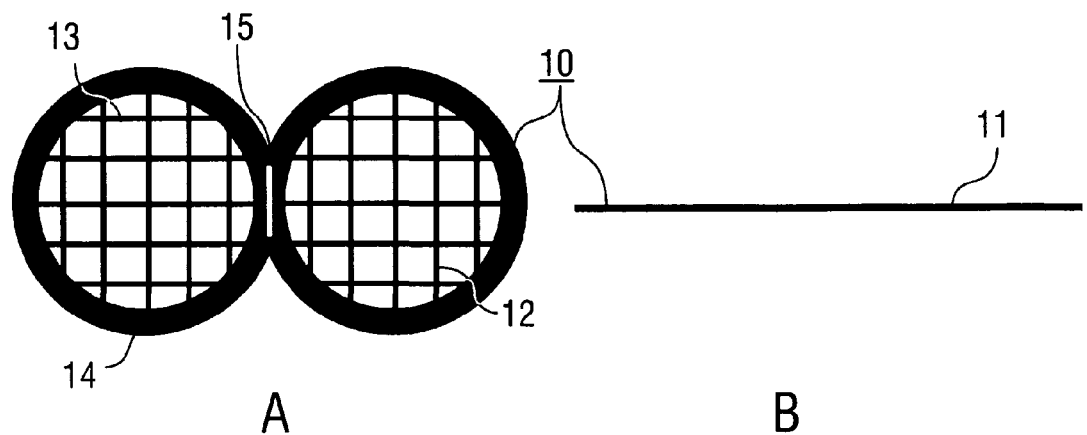
Figure 9:
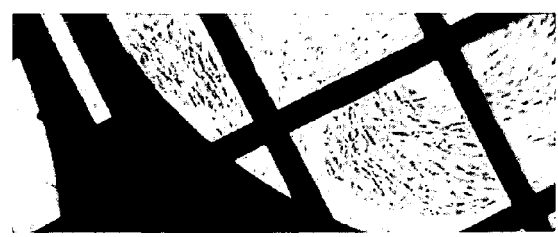
Figure 9:
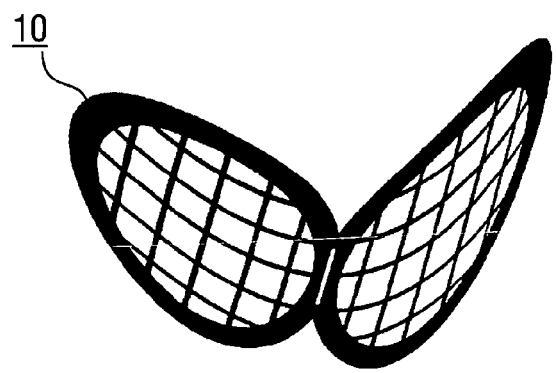

FIG. 9 shows a further lattice substrate 10, having a complex outer shape, in different phases of substrate deformation according to the invention (A: plan view; B: sectional view; C: photographic partial view; D: perspective view). In a first phase prior to the start of deformation, the lattice substrate 10 has a plane form (FIGS. 9A, B). The lattice frame 14 is composed of two circles between which is formed a bending region 15 with reduced flexural rigidity. The lattice elements 13 are arranged as a uniform rectangular lattice having identical thicknesses. After overgrowth with a cell arrangement made of rat stem cells, a curvature of the lattice substrate 10 about the bending region 15 was produced (FIGS. 9C, 9D).

Figure 10:
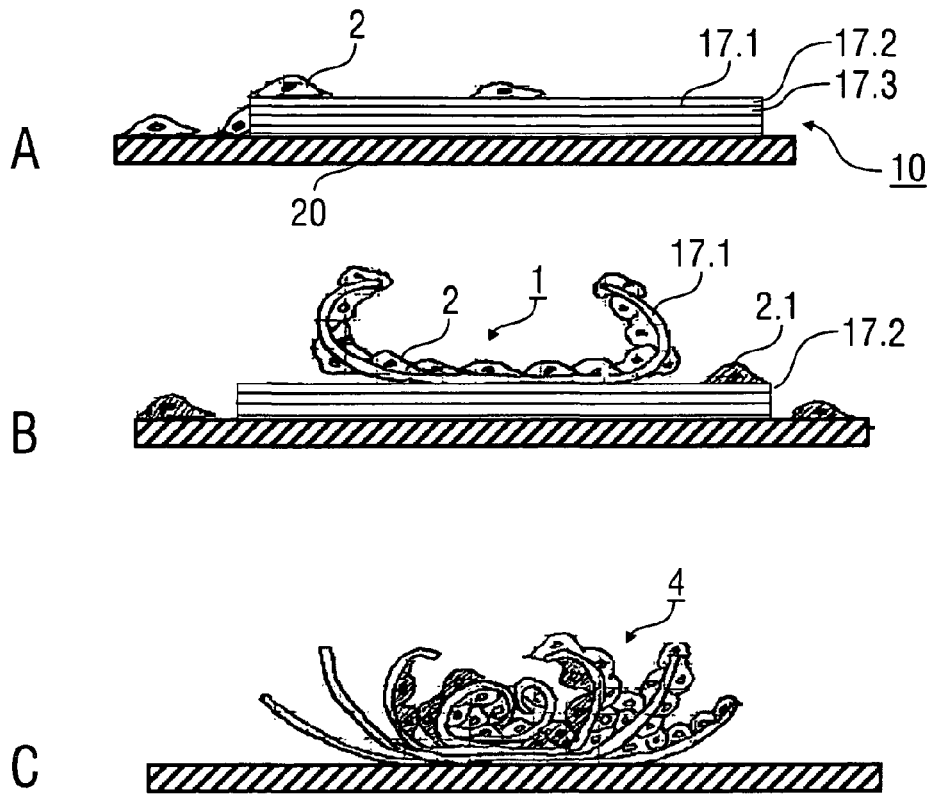
FIGS. 10 and 11: further embodiments of substrates according to the invention with a plurality of substrate parts.
Figure 11:
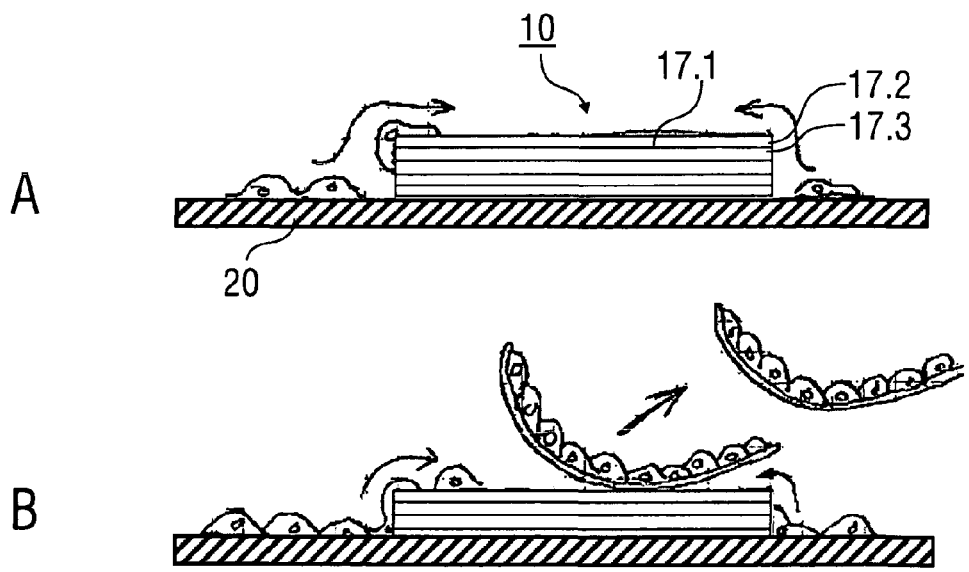

FIGS. 10 and 11 show two embodiments of the invention in which the substrate 10 comprises a stack having a plurality of substrate layers 17.1, 17.2, 17.3, . . . . The substrate layers 17.1, 17.2, 17.3, . . . comprise, for example, plastics films which are held together only by adhesive forces.

The embodiment of the formation, according to the invention, of a three-dimensional cell arrangement 1 as shown in FIG. 10 comprises the following steps. First, cells 2 are deposited on the uppermost substrate layer 17.1. Deposition techniques that are known per se, such as, for example, dropwise application using a pipette or, preferably as shown, the natural migration motion of adherent cells, are used for this. The adherent cells migrate, according to FIG. 10A, from a support 20 onto the uppermost substrate layer 17.1.

As soon as the number of cells 2 in the cell arrangement 1 on the uppermost substrate layer 17.1 is large enough for an adequately powerful attractive force to be exerted, the uppermost substrate layer 17.1 undergoes curvature. In this second phase (FIG. 10B) further cells of the same or a different type migrate onto the second substrate layer 17.2, which is again deformed. As the process progresses, the layered substrate 10 takes on a predetermined configuration as a result of the overgrowth of the cells and the attractive force exerted by the cells. The configuration is defined by the distribution of flexural rigidity in the individual substrate layers. As a result, the cell arrangement 1 shown by way of example in FIG. 10 is formed as a complex three-dimensional pile of cells 4 (cell aggregate) consisting of layers of a single cell type or of different cell types. Advantageously, cell arrangements of this kind can be used, in particular, as co-culture systems or as a tissue model in tissue engineering.

FIG. 11 shows an alternative variant of the use of a substrate 10 consisting of a plurality of substrate layers 17.1, 17.2, 17.3, . . . . The cells 2 first migrate onto the uppermost substrate layer 17.1 (FIG. 11A) which, after adequate overgrowth, undergoes deformation and can be separated from the substrate layer 17.2 disposed therebelow (FIG. 11B).

The method illustrated in FIG. 11 enables layered substrates 10 having a plurality of substrate layers to be used for producing germs populated with cells for trypsin-free propagation. The populated substrate layers, separated from the remaining substrate 10 and transferred to new culturing vessels, can be used as germs for further proliferation of the cells without the use of trypsin.

Figure 12:
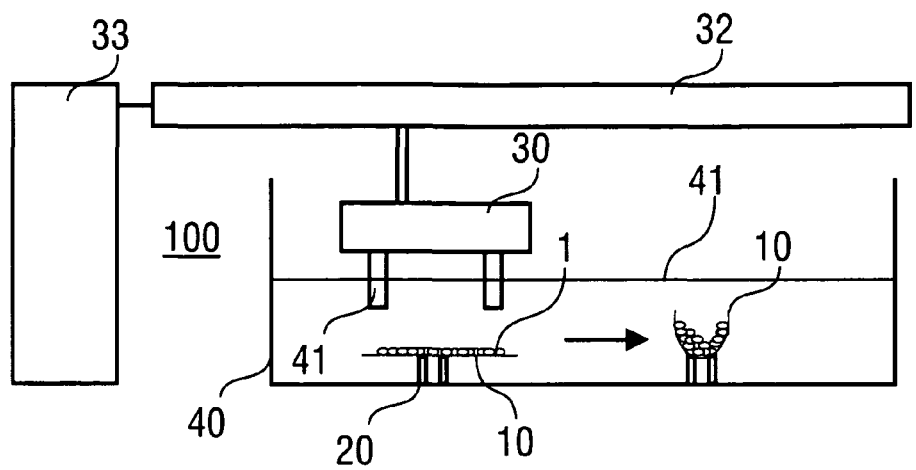
FIG. 12: a diagrammatic illustration of culturing apparatus.
Figure 13:
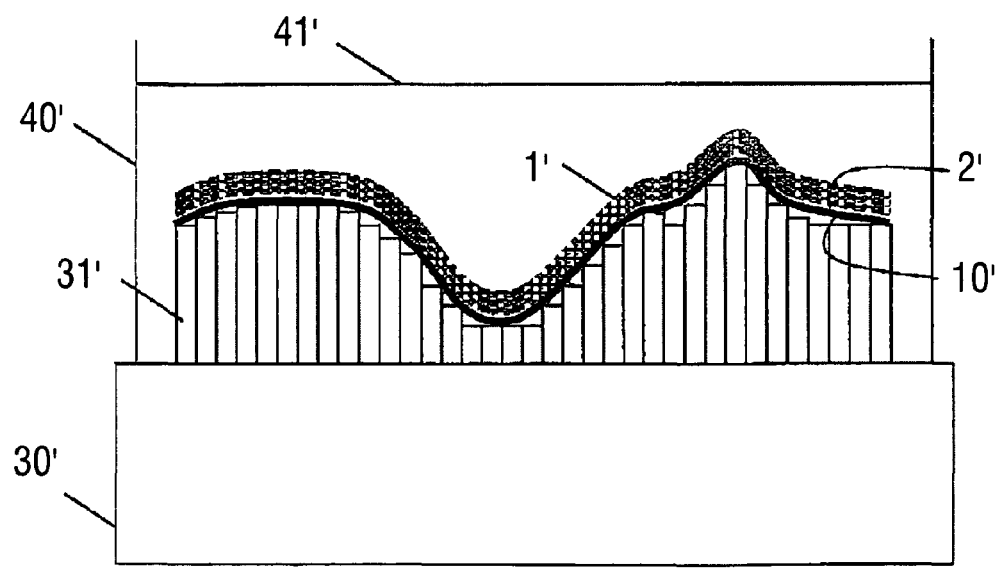
FIG. 13: an illustration of a conventional method for forming a three-dimensional cell arrangement (prior art).

FIG. 12 shows, by way of example, a culturing apparatus 100 with which the method according to the invention is preferably carried out. The substrate 10 according to the invention is arranged on a support 20 in a culturing vessel 40 containing a liquid culturing medium 41. Under the action of the attractive force in the cell arrangement 1, the substrate 10 is deformed, as shown in the right-hand partial image in FIG. 12. FIG. 12 also shows a tool 30 for exerting an external deformation force on the substrate 10. The tool 30 comprises, for example, two pointed tool elements 31 with which there is exerted, at borders of the substrate 10, a force which assists the attractive force of the cells. The tool 30 is connected to a positioning system 32 and a controlling element 33.

With the above-described shape changes of substrates according to the invention and/or the combination of a plurality of deformed substrates it is possible, according to the invention, to form multilayer cell systems which advantageously have numerous uses in cell biology, in medical therapy or in tissue engineering. For example, multicellular spheres (FIG. 4) can be used as tissue models for what are known as organoid bodies. Hollow shapes can enclose biological active ingredients, biological materials such as, for example, differentiation factors or cell components. Organoid structures can be replicated for tissue engineering functions.

The use of slowly resorbable materials, in particular as a lattice substrate, allows the production of three-dimensional cell systems which have a defined shape and which retain their shape after resorption of the material. Three-dimensional cell arrangements of this kind are suitable, in particular, for implantation in an organism.

Combining separately produced cell structures also makes it possible to produce three-dimensional cell arrangements which have layers consisting of different cell types and which can, in particular, be used as a co-culture system or tissue model. Cell arrangements of this kind can be manually combined or can be produced by folding layered substrates (FIG. 10). Furthermore, coating the substrate according to the invention with a modification layer, in particular with bioactive molecules, makes it possible for cell differentiation to be induced, for coating-specific population with different cell types to be produced or for an artificial stem cell niche to be created.

The features of the invention disclosed in the above description, the drawings and the claims may be significant, individually or in combination, for the performance of the invention in its different developments.

The invention claimed is:

1. A method for forming a three-dimensional cell arrangement of biological cells, comprising the steps of:
    providing cells which are cultured in an arrangement on a flexible substrate, which is capable of both cell adhesion and being deformed by the attractive force exerted by the cells;
    allowing the cells to exert an attractive force on the substrate that deforms the substrate, wherein the substrate curves to provide a deformed substrate having a tubular shape or a spherical shape.

2. The method according to claim 1, wherein the deforming comprises a bending of the substrate such that the cell arrangement forms a spatially curved planar layer of cells.

3. The method according to claim 1, wherein the deforming comprises a folding of the substrate such that the cell arrangement forms a three-dimensional pile of cells.

4. The method according to claim 1, wherein the cells are adherently arranged on a substrate surface of the substrate and form a continuous layer of cells.

5. The method according to claim 1, wherein a directional deformation of the substrate is provided with at least one predetermined main deformation direction.

6. The method according to claim 5, wherein the at least one main deformation direction is determined by a predetermined geometric arrangement of at least one of deformation regions and force action points of the substrate.

7. The method according to claim 1, wherein the deforming of the substrate comprises a shape change of at least one substrate part, wherein at least one of a position and an alignment of the at least one substrate part relative to a remainder of the substrate is varied by the deforming.

8. The method according to claim 1, wherein the deforming of the substrate comprises: (a) a shape change of at least one planar substrate layer, or (b) a shape change of the at least one planar substrate layer and a separation of the at least one planar substrate layer from a remainder of the substrate.

9. The method according to claim 1, further comprising at least one of the following steps:
    supplying further cells to the cell arrangement,
    dissolution and/or removal of the substrate, and
    joining of a plurality of deformed substrates.

10. The method according to claim 9, wherein deforming of the substrate and forming of the cell arrangement take place while or after the cells are cultured.

11. The method according to claim 1, wherein there acts upon the substrate at least one additional deformation force which comprises at least one of an external mechanical force and an internal reaction force in a material of the substrate.

12. The method according to claim 1, wherein the substrate:
    is made from at least one of plastic, metal and a resorbable material, or
    has a continuous substrate surface, or
    has a substrate surface broken by holes or depressions, or
    has a lattice structure, or
    has a modification layer.

13. The method according to claim 1, wherein only a portion of the substrate curves.

* * * * *